(12) United States Patent
Kunath-Fandrei

(10) Patent No.: US 8,567,948 B2
(45) Date of Patent: Oct. 29, 2013

(54) DEVICE AND METHOD FOR EXAMINING THE EYE FUNDUS, ESPECIALLY THE PHOTORECEPTORS

(75) Inventor: Gerald Kunath-Fandrei, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 780 days.

(21) Appl. No.: 12/680,470

(22) PCT Filed: Sep. 16, 2008

(86) PCT No.: PCT/EP2008/007702
§ 371 (c)(1),
(2), (4) Date: Mar. 26, 2010

(87) PCT Pub. No.: WO2009/043475
PCT Pub. Date: Apr. 9, 2009

(65) Prior Publication Data
US 2010/0238401 A1   Sep. 23, 2010

(30) Foreign Application Priority Data

Sep. 28, 2007 (DE) .......................... 10 2007 047 460

(51) Int. Cl.
*A61B 3/14* (2006.01)

(52) U.S. Cl.
USPC .......................................... 351/207; 351/246

(58) Field of Classification Search
USPC .......................................... 351/205, 207, 246
See application file for complete search history.

(56) References Cited

U.S. PATENT DOCUMENTS

| | | | |
|---|---|---|---|
| 4,423,931 A | 1/1984 | Shapiro | |
| 5,116,115 A | 5/1992 | Lange et al. | |
| 5,867,604 A | 2/1999 | Ben-Levy et al. | |
| 6,376,818 B1 | 4/2002 | Wilson et al. | |
| 2008/0166041 A1 | 7/2008 | Wolleschensky | |
| 2008/0192203 A1 | 8/2008 | Biernat et al. | |
| 2008/0278686 A1* | 11/2008 | Kasper et al. | 351/207 |
| 2009/0268280 A1 | 10/2009 | Osawa et al. | |

FOREIGN PATENT DOCUMENTS

| | | |
|---|---|---|
| CA | 2 284 299 A1 | 3/2001 |
| DE | 36 21 983 A1 | 1/1988 |
| DE | 698 02 514 T2 | 6/2002 |

(Continued)

OTHER PUBLICATIONS

Neil, M.A.A., et al., "Method of obtaining optical sectioning by using structured light in a conventional microscope," *Optics Letters*, vol. 22, No. 24 (Dec. 15, 1997), pp. 1905-1907.

(Continued)

*Primary Examiner* — James Greece
(74) *Attorney, Agent, or Firm* — Patterson Thuente Pedersen, P.A.

(57) ABSTRACT

A device for examining the eye fundus and photoreceptors includes an illumination beam path having optical beam forming and/or guiding components, at least one illumination unit for providing a continuous illumination and a flash illumination, and an observation and imaging beam path having optical beam forming and/or guiding components and a device for varying the magnification, including a beam splitter for splitting the observation and imaging beam path. A rotatable diffraction grating is disposed in a plane in the observation and imaging beam path that is conjugate to the object plane and the movement of the grating is synchronized with the illumination unit that serves as the flash illumination so that an image recording sensor records a rapid sequence of images of the eye fundus at different positions of the grating and said sequence is forwarded to an existing evaluation unit.

14 Claims, 1 Drawing Sheet

(56) References Cited

FOREIGN PATENT DOCUMENTS

| | | |
|---|---|---|
| DE | 10 2005 030 228 A1 | 1/2007 |
| EP | 0 554 643 A1 | 8/1993 |
| EP | 1 248 132 A2 | 10/2002 |
| EP | 1 412 804 | 2/2003 |
| EP | 1 992 276 A1 | 11/2008 |
| WO | WO 96/24082 | 8/1996 |
| WO | WO 98/45745 | 10/1998 |
| WO | WO 00/43819 | 7/2000 |
| WO | WO 2005/044098 A1 | 5/2005 |
| WO | WO 2007/036304 A2 | 4/2007 |
| WO | WO 2007/043314 A1 | 4/2007 |

OTHER PUBLICATIONS

Yoshimura, Takeaki, et al., "Topographic Analysis of Ocular Fundus Using the Fourier Transform Method for Projected Grating Images," *Optical Review* vol. 2, No. 5, (1995), pp. 388-393.

Gustafsson, M.G.L., "Surpassing the lateral resolution limit by a factor of two using structured illumination microscopy," *Journal of Microscopy*, vol. 198, Pt. 2 (May 2000), pp. 82-87.

Bindewald, A., et al., "cSLO Fundus Autofluorescence Imaging. Methodical Advancement of Confocal Scanning Laser Ophthalmoscopy," *The Ophthalmologist*, Mar. 2005, Pt. 102, pp. 259-264.

Starkey, Douglas E., et al., "Image Projection Optical System for Measuring Pattern Electroretinograms," *Proc. SPIE*, vol. 2126, Jun. 1994, pp. 271-282.

\* cited by examiner

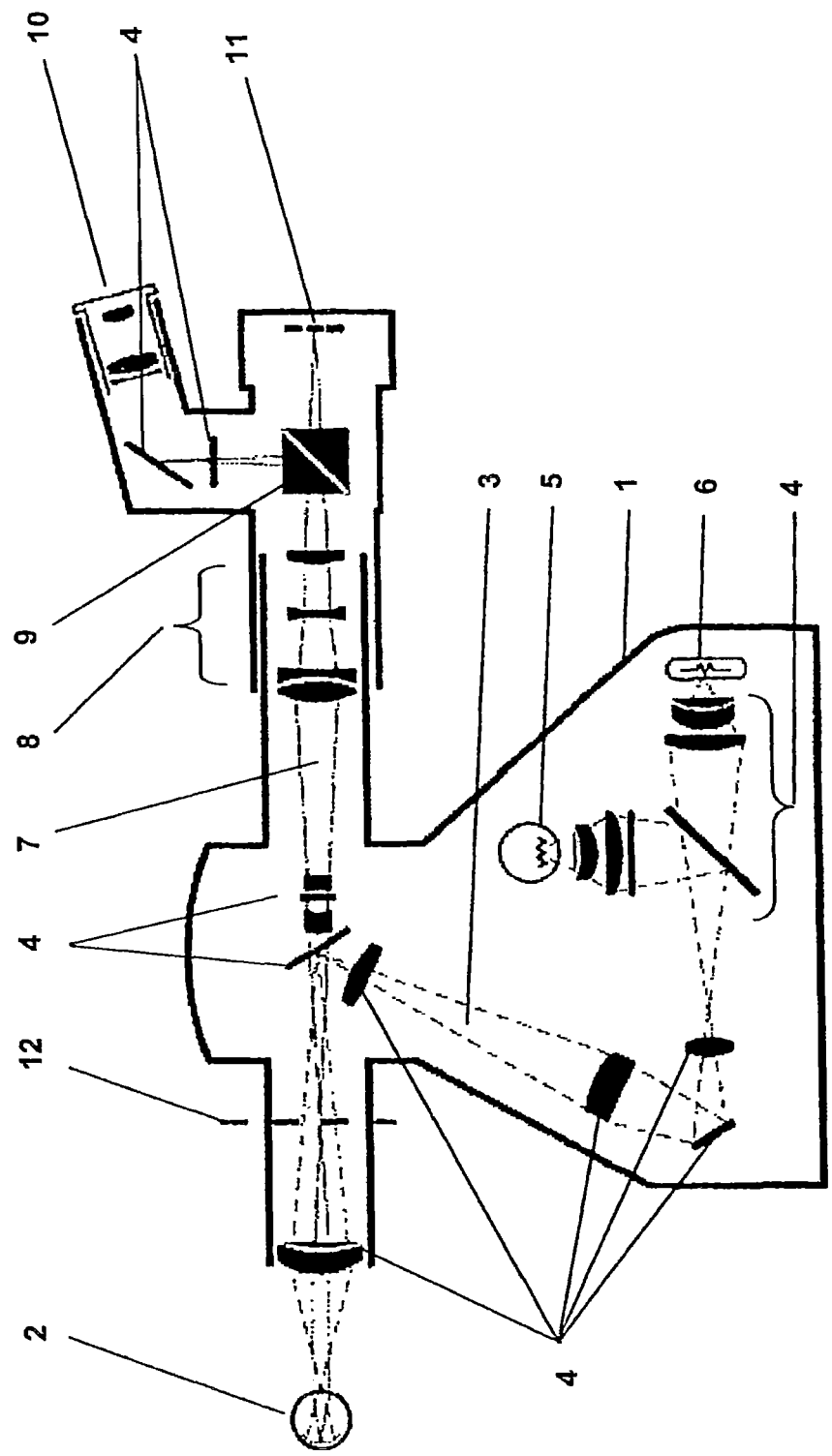

DEVICE AND METHOD FOR EXAMINING THE EYE FUNDUS, ESPECIALLY THE PHOTORECEPTORS

PRIORITY CLAIM

The present application is a National Phase entry of PCT Application No. PCT/EP2008/007702, filed Sep. 16, 2008, which claims priority from German Application Number 102007047460.3, filed Sep. 28, 2007, the disclosures of which are hereby incorporated by reference herein in their entirety.

BACKGROUND OF THE INVENTION

The invention herein relates to a solution, which, in addition to the standard examinations of the eye fundus, allows for mapping and/or examination of the photoreceptors in the human eye in order to diagnose and treat diseases at an early stage. Changes of those light-sensitive sensory cells of an eye, called photoreceptors, are frequently the first signs of diseases. Thereby, an early detection drastically increases the chances for a successful treatment.

The human eye exhibits, for example, two types of photoreceptors: Rods and cones. While the light-sensitive rods allow for night vision, the cones allow for daylight vision and color sensitivity (red, blue, green).

The examination and evaluation of pathological changes of the visible part of the eye, particularly the retina and its blood-supplying vessels, are called ophthalmoscopy or funduscopy. Thereby, the vessels, which supply the retina with blood, are clearly distinguishable from the retina, whereby the light-red appearing arteries, which originate in the optic nerve papilla (blind spot), are also distinguishable from the dark-red appearing veins.

In ophthalmoscopy, two different methods are commonly applied. While the so-called direct ophthalmoscopy, whereby the ophthalmoscope is placed at a distance of approximately 10 cm, i.e., directly in front of the patient's eye, and achieves an angle of view of 10 to 15° with a magnification of up to 15 times, is better suited for examining details, such as optic nerve papilla, vessel origins, and the yellow spot (macula lutea), indirect ophthalmoscopy at a distance of approximately 50 cm with a magnification of 2 to 5 times and an angle of view of 25 to 40°, is better suited for the viewing and examination of the eye fundus as a whole. Most eye specialists prefer the indirect ophthalmoscopy because it provides a significantly better overview due to the smaller magnification and, unlike direct ophthalmoscopy, it allows for a stereoscopic (3D) evaluation. Furthermore, indirect ophthalmoscopy can also be performed with the slit lamp, known as a standard device for the examination of the eye by eye specialists. With a slit lamp the retinal image can be magnified and/or evaluated with an even greater 3D effect through projection of a slit of light. However, examination with a slit lamp is not suitable for observing details in the retina due to insufficient resolution of the lens system of a slit lamp.

In addition to ophthalmoscopy, OCT assemblies (Optical Coherence Tomography) are now commonly used for detailed optical examination of the eye fundus. OCT is an examination method, whereby temporally short coherent light is utilized with the help of an interferometer for distance measurement of the reflective materials to be found in the eye.

The basic principle of OCT is based on white light interferometry, whereby the durations of a signal are compared with each other with the help of an interferometer (most commonly, a Michelson interferometer). Thereby, one arm of the interferometer with known optical path length (=reference arm) is used as reference for the measurement arm.

The interference of the signals (optical cross correlation) from both arms results in an interference pattern from which the relative optical path length can be determined within an A-scan (individual depth signal). Subsequently, the beam in the one-dimensional raster scan is led transversally in one or two directions, whereby a two-dimensional B-scan or a three-dimensional tomogram (C-scan) can be obtained.

The preeminent feature of OCT is the decoupling of the transversal from the longitudinal resolution. In conventional light microscopy, the axial resolution (depth) as well as the transversal resolution depends on the focusing of the light beam. The parameter for the focusability is the numerical aperture. In OCT, the resolution is only restricted by the bandwidth of the applied light. Therefore, with great bandwidth (wide spectrum), a high resolution, with which small details can be resolved, is achievable.

The areas of application for OCT are primarily in medicine, particularly, ophthalmology, as well as for early cancer diagnosis and skin examinations. Thereby, reflections are measured at boundaries of materials with varying refractive indices and, subsequently, a three-dimensional image is reconstructed. Such a reconstruction is called tomography.

Currently, the main application is the examination of the eye fundus and/or the posterior eye segment since competing technologies, such as the confocal microscope, can only insufficiently map the fine layer structure of the retina with its thickness of approximately 250-300 µm due to the small size of the pupil and the great distance between cornea and retina. Most of all, the significant advantage of OCT is the contact-free measurement since risks of infection and emotional stress are largely avoided.

A further commonly used method for detailed optical examination of the eye fundus is fundus autofluorescence (FAF). With this method, lipofuscin accumulation can non-invasively be detected in vivo in the lysosomal compartment of the single-layered retinal pigment epithelium (RPE).

In [1], A. Bindewald et al. describe a further developed method for scanning laser ophthalmoscopy.

Thereby, resolutions of up to 5 µm/pixel are achieved with the use of confocal scanning laser ophthalmoscopes (cSLO) on the basis of solid-state lasers for generating excitation laser light (488 nm), causing changes of the topographical FAF intensity distribution to appear in different retinal pathologies, including age-related macular degeneration, macular edema, and genetically determined retinopathies. Internal fixation control, magnification of the focus area, improved lens system, and a new laser source result in advantages for clinical applications. Improved quality of FAF images with the new cSLO is of importance for clinical diagnostics and the precise phenotyping of retina diseases for scientific purposes as well as for future therapy monitoring on RPE cell basis.

With the methodical advancement of confocal scanning laser ophthalmoscopy, FAF images of hitherto unknown quality are produced, which even allows for the differentiation of individual RPE cells in vivo. Aside from reliable findings with prior applications, possibilities for new therapeutic methods also arise.

The disadvantages of both methods lie in the facts that they are not based on standard devices commonly used by eye specialists as well as their extremely high costs.

The slit lamp as well as the fundus camera are considered conventional standard devices for eye specialists. While the slit lamp more commonly applies to the examination of the anterior eye segments, the fundus camera is designated for the examination of the eye fundus.

Thereby, fundus cameras, which are equipped with image registration units for documentation, are commonly used. Pictorial representation of the retina of the human eye is an important aid for diagnoses. However, the technical realization of images of the eye fundus is no trivial matter due to the optical structure of the eye.

Thereby, new methods forgo the use of pupil-dilating measures on the patient and work with infrared illumination. The quality of the findings images essentially depends on the optical positioning of the fundus camera, however, the optical properties of the eye itself, as part of the imaging optical path, limit the achievable results. Advanced fundus cameras are equipped not only with a digital imaging unit but also with image processing and archiving systems. For the examination of the eye fundus with fluorescent solutions, which are added to the patient's blood, applicable excitation and band-elimination filters are present in the optical path, which are swiveled into the optical path, if needed.

Since the viewing angle of classic fundus cameras is approximately 60°, detailed examinations of the photoreceptors in the human eye are not possible because the resolution of their lens systems is insufficient for said purpose.

By means of optical adjustments, the conventional viewing angles of 45 to 60° for fundus imaging could be decreased, thereby allowing for mapping of smaller segments of the human retina with corresponding higher resolution. But the structures of the photoreceptors cannot be made visible even with higher resolution because the depth of field of the fundus camera is too low. In order to map the photoreceptors of the human retina, transverse resolutions of less than 5 µm are required. Furthermore, the additionally mapped out-of-focus layers of the retina during fundus imaging with a fundus camera have further adverse effect on the imaging quality.

In [2] and WO 1996/24082 A1, Gustafsson describes that in a fluorescence microscope the lateral resolution can be magnified by a factor of two by illuminating the sample with a spatially structured light source.

Through illumination with a series of excitation patterns, high-resolution information, which is usually inaccessible, is encoded into the observed image. The stored images are processed linearly in order to extract the new information and produce a reconstruction with double resolution. Unlike confocal microscopy, the entire emission light is used, producing images with greater clarity when compared to confocal microscopy.

According to prior art, solutions are also known, whereby the sample to be examined is illuminated with periodic patterns in order to achieve an increase in resolution.

The solution described in U.S. Pat. No. 5,867,604 A relates to a system for the improvement of the resolution of imaging systems by means of illumination with a periodic pattern. Thereby, particularly the illumination phase is altered in order to extract the amplitude and the phase data from the received scattered light images and produce synthetic three-dimensional images. The periodic illumination patterns can be produced from diffraction gratings as well as by interferometric means. In a particularly advantageous embodiment, the application of the described method in a confocal microscope is described.

WO 1998/045745 A1 also describes a solution which relates to a system for the improvement of the resolution of imaging systems by means of illumination with periodic patterns. Thereby, the illumination pattern is moved continuously or discretely, so that at least three images of the sample can be produced with varying phasing of the illumination pattern. An evaluation unit removes the spatial patterns from the images, resulting in an image of the sample which is optically divided into sections. In a particularly advantageous embodiment, the application of the described method in a conventional microscope is described.

Even though both descriptions contain references regarding the application of the solutions for other optical imaging systems, a specific application, as, for example, in ophthalmology, is not mentioned.

In U.S. Pat. No. 5,116,115 A, a method and an assembly for measuring the topography of the cornea of an eye is described. Thereby, a thin, flexible, reflecting material is placed in such a way on the cornea to be examined that it adjusts exactly to the shape of the cornea. As a result, it is possible to capture the shape of the cornea by means of the projected pattern. For said purpose, structured sinusoidal patterns with varying phasings are projected onto the cornea and mapped by a detector. A computer calculates an elevation map from the digitalized images at various phasings. By means of the calculated elevation map, the topography of the cornea can be viewed. The basic idea of this described solution consists of the determination of the topography of the cornea of an eye. Once again, no references are disclosed or implied with regard to other applications for the eye.

Methods and assemblies for microscopic imaging, whereby objects are illuminated from a light source with periodic patterns, are described in U.S. Pat. No. 6,376,818 B1 and EP 1 412 804 B1. Thereby, the periodic pattern consists of a striped pattern. By means of a microscope, at least three images of the object are mapped at varying spatial phasings and transmitted to an evaluation unit. From the analysis of those three images, a three-dimensional image of the volume structure of the object is derived, which generally only contains in-focus details. With the suggested solution, an assembly and method for producing three-dimensional images of an object to be examined are provided, which, similar to the confocal images, essentially only contain in-focus details.

Even though the description contains a reference regarding, particularly, the biomedical application of the solution, a specific application as, for example, in ophthalmology, is not mentioned.

In [3], Douglas Starkey describes an optical projection system for the detection of glaucoma diseases. In this solution, modifiable patterns, produced by an interferometer, are projected onto the retina of the eye to be examined. The electric potentials, which result from light impinging on the retina, are recorded with the help of electrodes as electroretinogram (ERG). The ERG shows the sum of the responses of the entire retina. The projection of certain patterns onto the retina allows, particularly, for the evaluation of the inner layers of the retina. Thereto, Starkey developed a device with which sinusoidal patterns are produced by means of a laser interferometer and projected onto the retina. The thereby recorded electroretinogram is also called PERG (pattern electroretinogram). While previously applied solutions were depicted by means of projectors or TV screens, the patterns in Starkey's solution are produced by a laser interferometer, including changes with regard to contrast, intensity, and spatial/temporal frequency. This allows for a significant reduction of distortions as well as chromatic deviations.

The modifiable patterns produced by Starkey are used exclusively for producing electroretinograms, particularly, PERG. No references are disclosed or implied with regard to other applications for the eye.

LITERATURE

[1] Bindewald, A., et al. *cSLO Fundus Autofluorescence Imaging. Methodical Advancement of Confocal Scanning Laser Ophthalmoscopy.* The Ophthalmologist 3/2005, Pt. 102, pp. 259-264.

[2] Gustafsson, M. G. L. *Surpassing the Lateral Resolution Limit By A Factor of Two Using Structured Illumination Microscopy*. Journal of Microscopy, Vol. 198, Pt. 2, 2000, pp. 82-87.

[3] Starkey, Douglas E.; Taboada, John; Peters, Daniel. *Image Projection Optical System For Measuring Pattern Electroretinograms*. Proc. SPIE Vol. 2126, 06/1994, pp. 271-282.

SUMMARY OF THE INVENTION

The invention herein overcomes the disadvantages of prior art and, in addition to conventional examinations of the eye fundus, also allows for mapping and/or examination of the photoreceptors in the human eye, whereby the solution shall be based on a conventional standard device used by eye specialists.

According to the invention, the solution for the examination of the eye fundus as well as photoreceptors in the human eye includes an illumination optical path, which, in addition to optical components for beam forming and/or guidance, exhibits at least one illumination unit for realizing a continuous and a flash illumination, as well as an observation and imaging optical path, which, in addition to optical components for beam forming and/or guidance, also exhibits a device for modification of the magnification as well as a beam splitter for splitting of the optical path in the direction of the oculars and in the direction of the imaging sensor. Thereby, in a plane, conjugated with regard to the object plane and located in the observation and imaging optical path, an optical grid, pivotable to various positions, is provided, the movement of which is synchronized with the illumination unit which functions as flash illumination, so that images of the eye fundus at various positions of the grid can be mapped in quick succession by the imaging sensor and transmitted to an existing evaluation unit.

With the proposed technical solution, based on a fundus camera, an examination of the eye fundus as well as the photoreceptors in the human eye is possible. Even though the solution described herein is based on a fundus camera, the solution is, in principal, also applicable for other ophthalmological devices.

BRIEF DESCRIPTION OF THE DRAWING

In the following, the invention is further described by reference to an embodiment example. It is shown:

FIG. 1: The basic structure of a fundus camera, according to the invention.

DETAILED DESCRIPTION

According to the invention, the device for the examination of the eye fundus as well as photoreceptors in the human eye includes an illumination optical path, which, in addition to optical components for beam forming and/or guidance, includes at least one illumination unit for realizing a continuous and a flash illumination, as well as an observation and imaging optical path, which, in addition to optical components for beam forming and/or guidance, also includes a device for modification of the magnification as well as a beam splitter for splitting of the optical path in the direction of the oculars and in the direction of the imaging sensor. Thereby, in a plane, conjugated with regard to the object plane and located in the observation and imaging optical path, an optical grid, pivotable to various positions, is provided, the movement of which is synchronized with the illumination unit which functions as flash illumination, so that images of the eye fundus at various positions of the grid can be mapped in quick succession by the imaging sensor and transmitted to an existing evaluation unit.

The optical grid, present in the observation and imaging optic path, in one embodiment exhibits a periodic structure. The imaging sensor is designed in such a way that it allows for the mapping and transmission to the evaluation unit of 3 images of the eye fundus in quick succession, whereby the grid position is altered each time by 120°. In one embodiment, the imaging sensor is able to map the quick succession of images of the eye fundus at varying grid positions and transmit them to the evaluation unit within a time frame of less than 300 ms.

Thereto, FIG. 1 shows the basic structure of a fundus camera, according to the invention.

According to the invention, the fundus camera 1 for the examination of the eye fundus as well as photoreceptors in the human eye 2 consists of an illumination optical path 3, which, in addition to optical components for beam forming and/or guidance 4, exhibits an illumination unit 5 for realizing continuous illumination, and an illumination unit 6 for realizing flash illumination, as well as an observation and imaging optical path 7, which, in addition to optical components for beam forming and/or guidance 4, also exhibits a device for modification of the magnification 8 as well as a beam splitter 9 for splitting of the observation and imaging optical path 7 in the direction of the oculars 10 and in the direction of the imaging sensor 11. Thereby, in a plane, conjugated with regard to the object plane and located in the observation and imaging optical path 7, an optical grid 12, pivotable to various positions, is provided, the movement of which is synchronized with the illumination unit 6 which functions as flash illumination, so that images of the fundus of the eye 2 at various positions of the grid 12 can be mapped in quick succession by the imaging sensor 11 and transmitted to an evaluation unit (not shown herein). Thereby, illumination unit 5 for continuous illumination as well as illumination unit 6 for flash illumination are designed as white light source. In another embodiment, both illumination units 5 and 6 are designed as LED or LED array.

The images of the eye fundus of the eye 2, mapped in quick succession by the imaging sensor 11 at varying positions of the grid 12, are transmitted to the evaluation unit, which processes the images in order to extract new information and produce a reconstructed image with higher resolution.

According to the invention, with the method for the examination of the eye fundus as well as photoreceptors in the human eye, the eye to be examined is illuminated via an illumination optical path, which, in addition to optical components for beam forming and/or guidance, exhibits at least one illumination unit for realizing a continuous as well as a flash illumination, and is observed and/or mapped via an observation and imaging optical path, which, in addition to optical components for beam forming and/or guidance, also exhibits a device for modification of the magnification as well as a beam splitter for splitting of the optical path in the direction of existing oculars and in the direction of an imaging sensor. Thereby, images of the eye fundus are mapped in quick succession by the imaging sensor at varying positions of an optical grid, pivotable to various positions and located in a plane, which is conjugated with regard to the object plane and located in the observation and imaging optical path, and transmitted to an existing evaluation unit. Thereby, the grid, the object, and the intermediate focal plane are positioned in planes conjugated to each other (focus planes).

The movement of the optical grid, which, preferably, exhibits a periodic structure, is synchronized with the illumination unit which functions as flash illumination. Preferably, 3 images of the eye fundus are mapped in quick succession by the imaging sensor, whereby the grid position is altered each time by 120°, and transmitted to the evaluation unit.

Thereby, the imaging sensor is designed in such a way that the quick succession of images of the eye fundus is mapped within a time frame of less than 300 ms and transmitted to an existing evaluation unit.

In one embodiment of the method, the described procedural steps are executed with a modified fundus camera, whereby the continuous as well as the flash illumination is realized with white light. Preferably, the white light is produced by LED's or an LED array.

With the help of 3 short flashes of the illumination unit for the realization of the flash illumination and the appropriately synchronized movement of the grid, images at varying phasings of the grid are mapped and further processed by the evaluation unit.

The "grid contrast," visible in the detected image through superimposition of the grid structure and the object structure, is a measure for the "confocality" of the assembly. Only those areas of the object, which are within the focus plane of the lens, are structurally mapped. When, through a shift of the grid, the resulting contrast for every pixel is subsequently calculated, an optical profile of the object is obtained.

The detection of such structured images of the object is performed sequentially by the evaluation unit. Images of the eye fundus may be mapped at three various relative position phases of the grid. At a relative phase difference of 120° each between the individual images, the defocused part of the image can be removed by the evaluation unit with a simple algorithm, which, in turn, increases the shadow contrast of the detected object.

The algorithm for calculating the synthetic optical sectional image of the eye fundus corresponds with the calculation of the modulation depth of the object coded with the optical carrier frequency (grid frequency). For a rectangular grid, the following 3-phase algorithm is to be applied for minimizing the higher harmonic:

$$I_{section_{x,y}} = 2\frac{\sqrt{2}}{3}\left\{\sqrt{\left[I_{x,y}(o) - I_{x,y}\left(\frac{2\pi}{3}\right)\right]^2 + \left[I_{x,y}(o) - I_{x,y}\left(\frac{4\pi}{3}\right)\right]^2 + \left[I_{x,y}\left(\frac{2\pi}{3}\right) - I_{x,y}\left(\frac{4\pi}{3}\right)\right]^2}\right\}$$

whereby $I_{x,y}$ represents the intensity in the focal point (x,y) in the various images (phasings of the grid).

The result is an optical sectional image of the object comparable to known confocal techniques (SLO).

With the solution, according to the invention, a device and a method are provided which allow for examinations of the eye fundus as well as the photoreceptors of the human eye. The solution may be based on a fundus camera, which is considered a standard device for eye specialists, therefore allowing for a wide range of applications of the solution. On the basis of a structured illumination, which is produced through the use of a pivotable grid, an LED illumination, and a fast imaging unit, high-contrast images of the photoreceptors of a human eye can be produced even with a "simple" fundus camera. The high-contrast, in-vivo produced images of the photoreceptors exhibit great depth of focus and are definitely comparable with the optical sectional image of the object produced with known confocal techniques (SLO).

The invention claimed is:

1. A device for the examination of the eye fundus and the photoreceptors in the human eye, comprising:
   an illumination optical path, including first optical components for beam forming and/or guidance and at least one illumination unit that provides a continuous and a flash illumination;
   an observation and imaging optical path, including second optical components for beam forming and/or guidance, a magnification modification device and a beam splitter that splits the observation and imaging optical path in the direction of oculars and in the direction of an imaging sensor;
   an optical grid located in a plane, which is conjugated with regard to the object plane and located in the observation and imaging optical path, the optical grid being pivotable to various positions, movement of the optical grid being synchronized with the illumination unit functioning as flash illumination; and
   wherein the device maps a quick succession of images of the fundus of the eye at various positions of the grid onto the imaging sensor and transmits the images to an evaluation unit.

2. The device according to claim 1, wherein the optical grid within the observation and imaging optical path exhibits a periodic structure.

3. The device according to claim 1, wherein three images of the fundus of the eye are mapped in quick succession by the imaging sensor, and wherein a position of the grid is altered by 120° for each of the three images and the three images are transmitted to the evaluation unit.

4. The device according to claim 3, wherein the three images of the fundus of the eye are mapped in quick succession by the imaging sensor at various positions of the grid within a time frame of no more than 300 ms and transmitted to the evaluation unit.

5. The device according to claim 1, wherein the device for the examination of the eye fundus and the photoreceptors in the human eye is a fundus camera.

6. The device, according to claim 5, wherein the illumination unit is designed in such a way that the continuous and the flash illumination are based on a white light source.

7. A method of examination of the eye fundus and the photoreceptors in the human eye, comprising:
   illuminating the eye to be examined by an illumination optical path, which includes first optical components for beam forming and/or guidance and at least one illumination unit that provides a continuous and a flash illumination;
   observing or mapping the fundus and the photoreceptors by an observation and imaging optical path which includes second optical components for beam forming and/or guidance, a magnification modification device and a beam splitter that splits the observation and imaging optical path in a direction of oculars and in a direction of an imaging sensor;
   mapping images of the fundus of the eye in quick succession onto the imaging sensor at various positions of an optical grid, which is pivotable to the various positions and positioned in a plane, which is conjugated with regard to the object plane and located in the observation and imaging optical path; and transmitting the mapped images to an evaluation unit.

8. The method according to claim 7, further comprising synchronizing the movement of the optical grid with the illumination unit that provides flash illumination.

9. The method according to claim 7, further comprising utilizing a grid that exhibits a periodic structure.

10. The method according to claim 7, further comprising mapping three images of the fundus of the eye in quick succession by the imaging sensor; and altering the position of the grid by 120° between the mapping of successive images and transmitting the images to the evaluation unit.

11. The method according to claim 7, further comprising mapping the images of the fundus of the eye in quick succession by the imaging sensor at various positions of the grid within a time frame of less than 300 ms and transmitting the images to the evaluation unit.

12. The method, according to claim 7, further comprising having the evaluation unit utilize the following algorithm for calculation of a synthetic optical sectional image of the fundus of the eye, wherein Ix,y corresponds with the intensity in the focal point (x,y) in the various images:

$$I_{section_{x,y}} = 2\frac{\sqrt{2}}{3}\left\{\sqrt{\left[I_{x,y}(o) - I_{x,y}\left(\frac{2\pi}{3}\right)\right]^2 + \left[I_{x,y}(o) - I_{x,y}\left(\frac{4\pi}{3}\right)\right]^2 + \left[I_{x,y}\left(\frac{2\pi}{3}\right) - I_{x,y}\left(\frac{4\pi}{3}\right)\right]^2}\right\}.$$

13. The method according to claim 7, wherein the device is a fundus camera used for the examination of the eye fundus and the photoreceptors in the human eye.

14. The method according to claim 7, further comprising basing the continuous and the flash illumination on white light.

* * * * *